(12) United States Patent
Hochrein et al.

(10) Patent No.: US 10,770,174 B2
(45) Date of Patent: Sep. 8, 2020

(54) MONITORING SYSTEM FOR A DIALYSIS MACHINE

(71) Applicant: Fresenius Medical Care Deutschland GmbH, Bad Homburg (DE)

(72) Inventors: Torsten Hochrein, Eschenau (DE); Nadja Schubert, Schweinfurt (DE); Frank Hedmann, Volkach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 15/896,695

(22) Filed: Feb. 14, 2018

(65) Prior Publication Data

US 2018/0308573 A1    Oct. 25, 2018

(30) Foreign Application Priority Data

Apr. 24, 2017  (DE) .......................... 10 2017 206 877

(51) Int. Cl.
| | |
|---|---|
| *G16H 40/60* | (2018.01) |
| *A61M 1/28* | (2006.01) |
| *G16H 40/67* | (2018.01) |
| *G16H 40/40* | (2018.01) |
| *G16H 40/20* | (2018.01) |

(Continued)

(52) U.S. Cl.
CPC ............. *G16H 20/40* (2018.01); *A61M 1/28* (2013.01); *G16H 40/20* (2018.01); *G16H 40/40* (2018.01); *G16H 40/60* (2018.01); *G16H 40/67* (2018.01); *A61M 1/1601* (2014.02);

(Continued)

(58) Field of Classification Search
CPC combination set(s) only.
See application file for complete search history.

(56) References Cited

U.S. PATENT DOCUMENTS

| | | | |
|---|---|---|---|
| 5,629,871 A | * | 5/1997 | Love .................. A61M 1/16 702/34 |
| 6,406,426 B1 | | 6/2002 | Reuss et al. |

(Continued)

FOREIGN PATENT DOCUMENTS

DE    10 2014 017897 A1    6/2016

OTHER PUBLICATIONS

International Patent Application No. PCT/EP2018/060423, Search Report dated Jul. 9, 2018.

*Primary Examiner* — Hayden Brewster
(74) *Attorney, Agent, or Firm* — Leydig, Voit & Mayer, Ltd.

(57) ABSTRACT

The invention relates to a monitoring system for at least one dialysis machine (e.g. a peritoneal dialysis machine), wherein the monitoring system receives data from a dialysis machine to be monitored via a first data communication network, wherein the data are selected from a group comprising machine data, error codes, operational data, environmental data, consumables data, network data, treatment data, wherein the data received are stored in a manner which is specific to the respective peritoneal dialysis machine, wherein for each machine, at least individual components of the stored data are analyzed wherein, on the basis of the analysis, an action selected from informing a patient, informing a medical professional, informing service personnel, informing a quality management representative is carried out via a second data communication network.

19 Claims, 2 Drawing Sheets

(51) Int. Cl.
*G16H 10/60* (2018.01)
*A61M 1/16* (2006.01)
*G16H 20/40* (2018.01)

(52) U.S. Cl.
CPC .............. *A61M 2205/3553* (2013.01); *A61M 2205/3584* (2013.01); *A61M 2205/52* (2013.01); *G16H 10/60* (2018.01)

(56) References Cited

U.S. PATENT DOCUMENTS

2004/0027244 A9 2/2004 Menard
2014/0230071 A1 8/2014 Adam et al.
2016/0206800 A1 7/2016 Tanenbaum et al.

* cited by examiner

MONITORING SYSTEM FOR A DIALYSIS MACHINE

CROSS-REFERENCE TO RELATED APPLICATIONS

Priority is claimed to German Patent Application No. DE 102017206877.9, filed on Apr. 24, 2017, the entire disclosure of which is hereby incorporated by reference herein.

FIELD

The invention relates to a monitoring system for at least one dialysis machine.

BACKGROUND

Many people suffer from kidney insufficiency or from chronic or acute kidney failure. Although, kidney transplantation is possible in principle, the availability of suitable donor organs is limited and a transplant cannot be carried out for all patients. Thus, methods for washing the blood, known as dialysis, have been developed in the past. The dialysis procedure is characterized in that exchange of substances is carried out by means of a membrane. In this, the fluid to be purified is on one side of the membrane and a suitable dialysate is on the other side.

Various methods have been established in the past. They include hemodialysis, in which urea, ureic acid and other substances are dialysed out of blood using a semipermeable membrane and under the influence of osmotic pressure. Other methods are hemoperfusion, hemodiafiltration and hemofiltration.

Furthermore, the peritoneal dialysis method was also developed in the past. Peritoneal dialysis is also known as PD. The term "peritoneal dialysis" also encompasses various methods such as, for example, manual CAPD (continuous ambulatory peritoneal dialysis), APD (automated PD) or CCPD (continuous cycling PD), which is carried out continuously by machine, IPD (intermittent PD), NIPD (night-time intermittent PD), etc.

These methods are based on the fact that the peritoneum is a membrane which lines the abdominal cavity and has a good blood supply.

Because of its particular construction, the peritoneum can in fact be used as a "filter membrane." In this regard, a tube (catheter) is usually implanted in a patient's abdominal cavity. A dialysate is passed via this catheter into the abdominal cavity and left there for a certain period of time. Substances with small molecules can then pass out of the blood via the capillaries of the peritoneum into the dialysate because of the existing concentration gradient After a certain time, the dialysate has to be drained out and replaced with fresh solution.

In contrast to artificial membranes in blood dialysis, the peritoneum is also highly permeable to proteins, whereupon a significant loss of protein occurs.

However, peritoneal dialysis has been shown to be advantageous in many respects. In contrast to other dialysis procedures, peritoneal dialysis allows for lengthier maintenance of any remaining kidney function. In addition, complications are reported less frequently for peritoneal dialysis, because the circulation is stressed to a lesser extent. This is of major advantage for patients with heart problems. In principle, peritoneal dialysis can also be used by patients in their domestic environment, while hemodialysis is only available in specially equipped centres/practices/clinics.

Despite these advantages, peritoneal dialysis is not widespread. Among other things, this can be put down to the fact that reliable, trouble-free operation of the associated machines cannot be guaranteed. Among other things, this can be put down to the fact that the peritoneal dialysis machines suffer from wear and tear which depends on its use, inter alia.

SUMMARY

In an exemplary embodiment, the invention provides a monitoring system for at least one dialysis machine, such as a peritoneal dialysis (PD) machine. The monitoring system includes a processor and a non-transitory computer-readable medium having processor-executable instructions stored thereon, wherein the processor-executable instructions, when executed by the processor, facilitate: receiving data from a dialysis machine via a first data communication network, wherein the data includes machine data, error codes, operational data, environmental data, consumables data, network data, and/or treatment data; storing the received data in a manner which is specific to the peritoneal dialysis machine; analyzing at least individual components of the stored data; and selecting an action based on the analysis, wherein the action includes sending information to a patient, a medical professional, service personnel, and/or a quality management representative via a second data communication network.

BRIEF DESCRIPTION OF THE FIGURES

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Exemplary embodiments of the invention provide a monitoring system for peritoneal dialysis machines which can provide increased safety for patients.

In an exemplary embodiment, the invention provides a monitoring system for at least one dialysis machine, such as a peritoneal dialysis (PD) machine, wherein the monitoring system receives data from a dialysis machine to be monitored via a first data communication network, wherein the data are selected from a group comprising machine data, error codes, operational data, environmental data, consumables data, network data, treatment data, wherein the data received are stored in a manner which is specific to the respective dialysis machine, wherein for each machine, at least individual components of the stored data are analyzed wherein, on the basis of the analysis, an action selected from informing a patient, informing a medical professional, informing service personnel, informing a quality management representative is carried out via a second data communication network.

Exemplary embodiments of the invention will now be described in more detail with reference to the figures. It should be noted in this regard that various aspects are described which may respectively be deployed individually or in combination. This means that any aspect may be used in different embodiments of the invention unless explicitly stated to be a pure alternative.

Furthermore, for the purposes of simplicity, reference may be made to just one entity. Unless explicitly stated, however, the invention may also comprise a plurality of the entities in question. In this regard, then, the use of the words "a" and "an" should be understood to be simply an indication that at least one entity is used in a simple embodiment.

Figure 1:
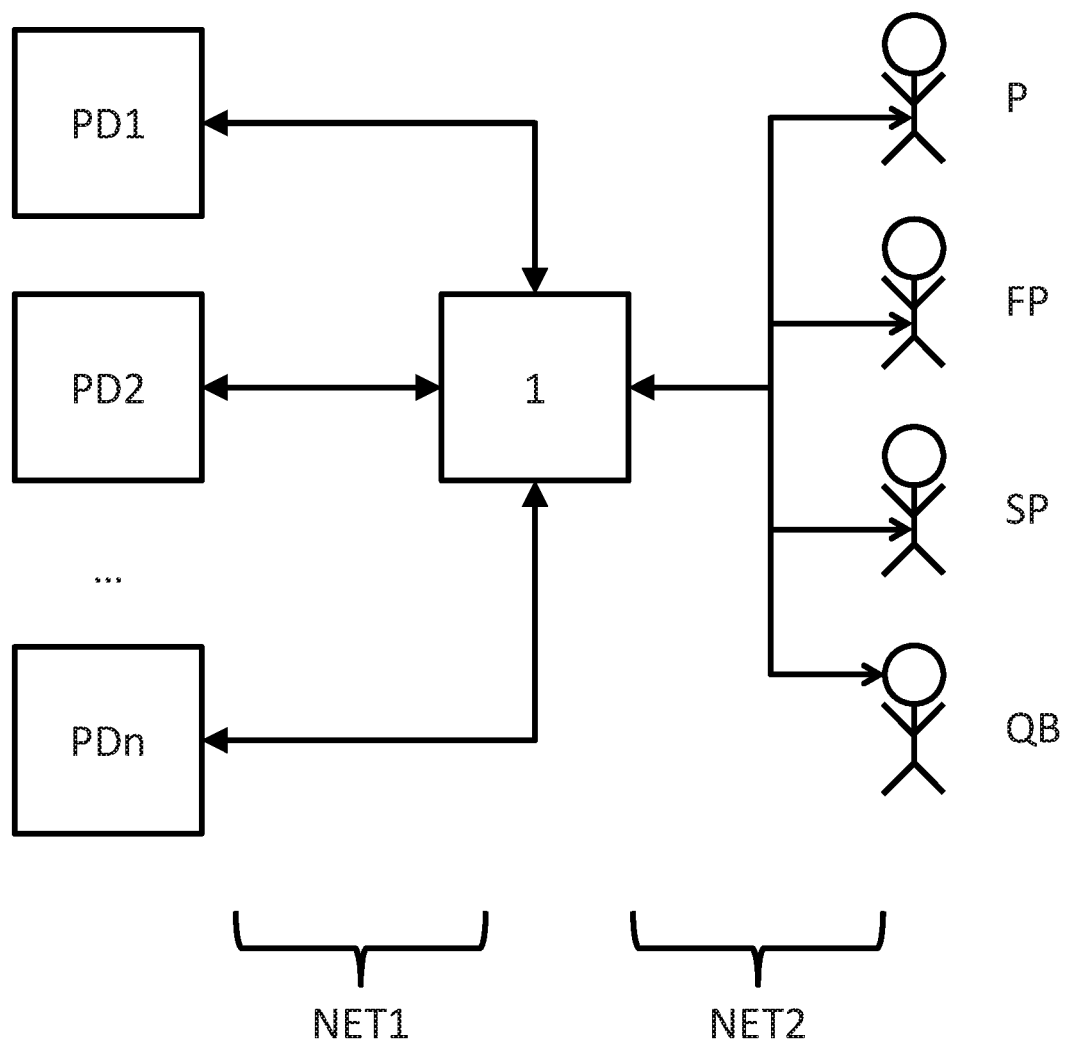
FIG. 1 shows a diagrammatic overview of a monitoring system and peritoneal dialysis machines in accordance with exemplary embodiments of the invention.

A monitoring system 1 in accordance with the invention is shown in its context in FIG. 1. The monitoring system 1 is suitable for monitoring at least one peritoneal dialysis machine PD1; in principle, however, it can also monitor a plurality of peritoneal dialysis machines PD1-PDn. Although the system described herein is discussed principally in connection with a peritoneal dialysis machine, it is also noted that the system described herein may be used, where appropriate, in connection with other types of medical devices, including, for example, hemodialysis machines.

Figure 2:
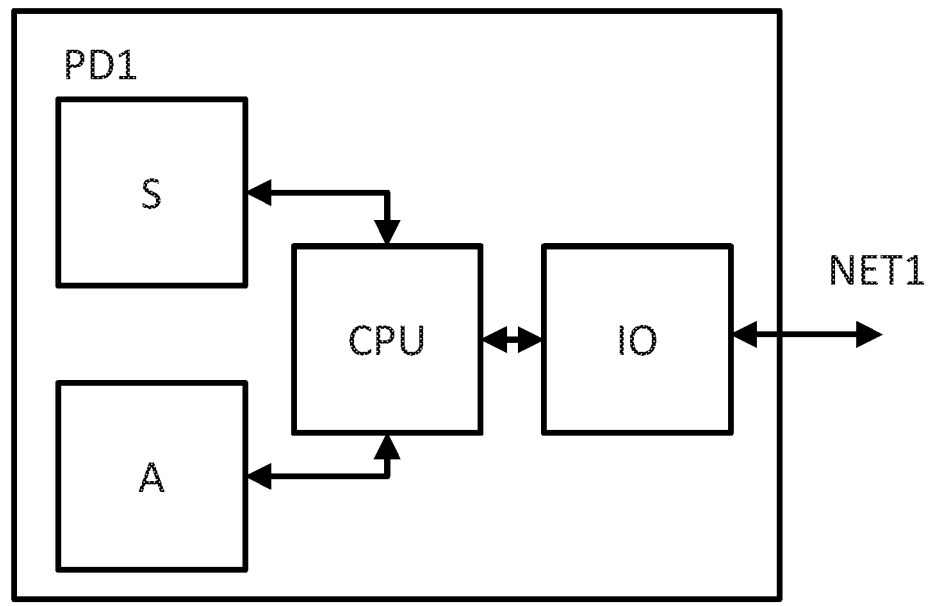
FIG. 2 shows a diagrammatic overview of components of a peritoneal dialysis machine in accordance with exemplary embodiments of the invention.

An example of a peritoneal dialysis machine PD1 is shown in FIG. 2. The peritoneal dialysis machine PD comprises, for example, one or more sensors S, one or more actuators A, at least one CPU (central processing unit) to process sensor data and/or to control the actuators A, as well as at least one communication unit IO which is configured to communicate with the respective first data communication network NET1.

The monitoring system 1 receives data from at least the one peritoneal dialysis machine PD to be monitored or from a selection or from all peritoneal dialysis machines PD1-PDn via a first data communication network NET1.

The data communication network NET1 may be any suitable wired or wireless data communication network. In addition, the transmission protocol for the respective implementation may be freely selected. In addition, the term "a data communication network" should not be construed in a limited manner, but different data communication networks may be provided for different data, or in fact redundant data communication networks may be provided. In addition, the mechanism for providing data may include active transmission via a user intervention at the peritoneal dialysis machine PD1, and/or periodic or event-related transmission of data via the peritoneal dialysis PD1 and/or interrogation of data by the monitoring system 1 (periodic, non-periodic, on request).

The data which is provided by the peritoneal dialysis machine PD1 or interrogated by it via the monitoring system 1 are selected from a group comprising machine data, error codes, operational data, environmental data, consumables data, network data, treatment data.

Figure 3:
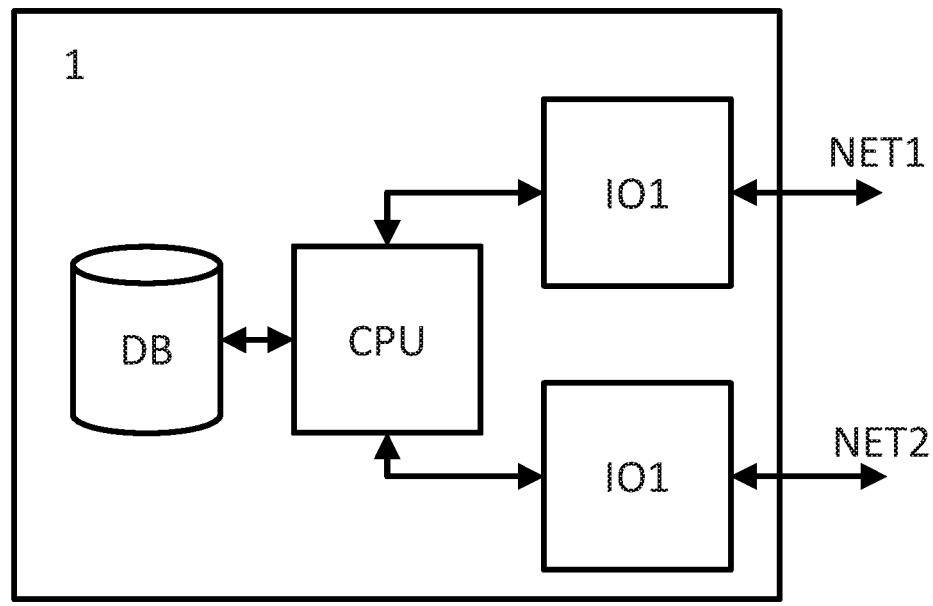
FIG. 3 shows a diagrammatic overview of components of a monitoring system in accordance with exemplary embodiments of the invention.

An exemplary monitoring system 1 is shown in FIG. 3. The monitoring system 1 comprises, for example, at least one CPU for processing data and a database DB or another local or remote data storage device, as well as at least one first logical communication unit IO1, which is configured for transmission to the respective first data communication network NET1, and a second logical communication unit IO2 which is configured for transmission to the respective second data communication network NET2.

It should be noted that the first data communication network NET1 and the second data communication network NET2 are shown as separate logical data communication networks. However, there is no imperative for the data communication networks to be different. Moreover, the first data communication network NET1 and the second data communication network NET2 may be components of one data network.

In the monitoring system 1, the data received from the peritoneal dialysis machine PD1 is stored in a manner which is specific to a respective peritoneal dialysis machine PD1, for example in a local or remote database DB or a local or remote data storage device.

In the monitoring system 1, then, at least individual components of the stored data can be analyzed in a machine-specific manner, whereupon on the basis of the analysis, an action selected from informing a patient P, informing a medical professional FP, informing service personnel (SP), informing a quality management representative QB is carried out via a second data communication network NET2.

As an example, this may be implemented in a manner such that the peritoneal dialysis machine PD1 provides the monitoring system 1 with machine and maintenance-related data via email or SMS. The monitoring system 1 extracts numerical values from the transmitted data. In the monitoring system 1, an analysis is carried out with a view to cases of faults, wear, as well as classifying the results with a view to severity of the fault and degree of wear.

As an example, faults are assigned an error code.

Routing to an appropriate user group is carried out as a function of the error code. This means that for every error code there is a clear referral to one or more user groups.

As an example, in the event of an fault which requires action by a service technician, the detected fault and the details of the faulty peritoneal dialysis machine PD1 are passed on to the service personnel SP.

As an example, a fault which could be traced to a lack of training of the user would be sent to a quality management representative. This may, for example, be a specific application adviser or even medical professionals such as physicians or nurses.

As an example, the data from the respective peritoneal dialysis machine PD1 may be sent to a central address/post box which is associated with the monitoring system 1. The monitoring system 1 then sorts the data received, for example according to sender (corresponds to the peritoneal dialysis machine). In this manner, the corresponding data is stored on the monitoring system 1 in a manner specific to a specific machine.

A WWW server may be provided on the monitoring system 1, for example. This may on the one hand prepare and display the data in a machine-specific manner (color coded and/or sorted), and on the other hand also carry out specific analyses upon the (machine-specific) data on request.

This means that in addition to active notification, it is also possible for specific user groups to carry out (machine-specific) analyzes on the data and to interrogate the results. In this regard, the results may be provided on the web server or in fact be sent via email/SMS to an address stored for the respective user to the appropriate recipient, for example the patient P, a physician and/or care personnel FP, service personnel SP, a quality management representative QB, and so on.

It should be noted that the analysis and notification functions may be constructed so as to be able to be configured.

As an example, serious faults may trigger an immediate response by service personnel SP. Other faults which are indicative of the occurrence of wear can be transmitted to the service personnel SP together with corresponding data and/or analyses. As an example, on the basis of the pressure profile of a membrane pump (recorded by a sensor S), it is possible to determine whether the over-pressure or under-pressure change is occurring within the appropriate ranges or at the appropriate rates. Furthermore, for example, the pressure profile can also be used to check whether the pressure is stable. Other and/or additional data can be used to determine whether the valves are opening/closing reliably. In addition, for example, an initialisation test could show that specific elements of the peritoneal dialysis machine are reaching their limits. Furthermore, for example, monitoring sensor zero points can determine the linearity of length sensors, etc. The number of degassing cycles can provide information regarding the seal of the hydraulic elements. In addition, for example, in general, the current consumption can be monitored. If this consumed current is comparatively high, this indicates an increased internal friction, for example loss of a lubricant, abrasion, etc. In addition, the general speed of individual components may be recorded. Here again, conclusions can be drawn regarding internal friction. In addition, the heat output can be recorded. If this increases, then this provides, for example, an indication regarding a fault in the heating system. Other data such as, for example, erroneous reading of barcodes, can be detected within a short period, indicative of a fault in the optical properties of a barcode reader subsystem of the peritoneal dialysis machine. Other parameters, such as data storage or electric batteries installed in the peritoneal dialysis machine, may also provide data regarding the condition.

This means that via the monitoring system 1 it is possible, by analyzing the data, to collect data regarding wear. In particular, for example, in a peritoneal dialysis machine PD to be monitored which has a membrane pump, it is possible to collect data regarding wear by analyzing changes in the pressure and/or channel profiles, i.e. profile data.

In one embodiment, the wear of the pump unit is determined using a pressure/channel profile of a membrane pump in the PD machine; the degree of wear is established as a function of changes in the recorded pressure/channel profile.

Although in the description above, emphasis has been placed on monitoring the peritoneal dialysis machine, the monitoring system 1 can also detect batch-to-batch variation in the disposable items used. Thus, for example, by analyzing the air detection, an indication can be provided regarding leaks in the various lines connected to the patient P.

Other sensors may also be present in the peritoneal dialysis machine in order, for example, to detect environmental conditions. Thus, for example, the environmental temperature may be determined in order, for example, to determine whether the heat output is in fact adequate. In addition, for example, the air pressure could be detected in order, for example, to be able to assess the performance of a compressor. The moisture in the air may also be determined in order, for example, to provide early detection of damage to the electronics, by corrosion by condensed moisture from the air. In addition, it is possible to monitor the mains electricity which provides energy to the peritoneal dialysis machine.

Other faults, however, indicate faulty training on using the peritoneal dialysis machine. Possible catheter problems could be detected by the number of "wake up" calls and/or by determining the rise in a dwell-time diagram. In addition, any shortfalls in the prescribed input volumes can be detected; these are an indication of a lack of compliance. In addition, switching points between infusion and drainage can be detected and be evaluated over a plurality of infusions. Here again, this could be an indication of lack of compliance. In addition, the general monitoring can be used to determine whether a treatment is in fact succeeding. From the number of error messages recorded, a conclusion may be drawn of lack of training on the peritoneal dialysis machine. Even the periods of time between providing a treatment and actual commencement of the treatment may be an indication of a lack of training, since too long a time interval may bring about contamination. In this case, for example, a quality management representative QB could be informed who would initiate fresh training of the patient P.

The appropriate trigger mechanisms may be designated on the monitoring system 1. As an example, the trigger parameters may be specified. In addition, it is possible to designate the persons to be contacted or the manner of contact. In this regard, specific persons and/or machines may be grouped so that, for example, the same parameters always belong to specific patients or specific machines.

However, the profile of the data to be transmitted from the monitoring system 1 to the relevant peritoneal dialysis machines could be designated.

From the machine data, the server determines a machine-specific evaluation as to which of the technical data and therapy data are to be extracted and viewed:
 hours of operation;
 durational data;
 machine faults with fault statistics;
 process parameters such as, for example, pump parameters, measurement results from initial tests, sensor values, etc.;
 displayed screen profile;
 total infusion/drainage dwells;
 total dwell times;
 infusion reduction;
 dwell time reduction;
 UF (ultrafiltration) measures (such as UF rate or UF volume).

The rules for analysis are integrated into the server and allow the server to interrogate the machine data for specific results or patterns.

As an example, the following data may be used:
 environmental conditions;
 state of repair (wear data, hours of operation, technician input, replaced components, equipment code, machine faults).

Various conclusions for the machine can be determined from this analysis:
 repair recommendations for servicing technicians;
 adjustments to the recording parameters for the machine;
 more detailed conclusions regarding batch-to-batch variation of disposable items;
 trend identification of component failure of machines;
 adjusting treatment or patient care;
 wear behavior of machine.

The data received is stored in the database DB, preferably linked to the time.

If faults occur more often within a specific time period, then additional data can be requested by the monitoring system 1 from the respective peritoneal dialysis machine in order to allow a more detailed analysis to be carried out.

From the frequency within a specific time period (fault rate), for example, an estimation can be made as to whether a fault is acute or how urgently a fault in the machine has to be corrected.

If faults occur less often within a specific time period, then less data can be requested by the monitoring system 1 from the respective peritoneal dialysis machine in order to allow a less detailed analysis to be carried out.

From the data received from the peritoneal dialysis machine, the monitoring system 1 filters out individual or multiple specific items of machine data and durational data and stores it.

A unique machine number, a unique number for the hardware with which the peritoneal dialysis machine is equipped, a unique identifier for the version of the software that is actually installed, the state to which the peritoneal dialysis machine was delivered, the language with which the peritoneal dialysis machine is delivered as well as the production date and the latest date a service technician was deployed to the peritoneal dialysis machine are included in the specific machine data.

The durational data contain the hours of operation of the peritoneal dialysis machine since delivery, the hours of operation of the peritoneal dialysis machine since the last service as well as the number of switching procedures for the valves, motors and heaters since delivery of the peritoneal dialysis machine.

In addition, the number of treatments can be determined from all of the data available for the monitoring system 1.

The specific machine data are extracted for analysis, inter alia, as to whether specific fault patterns exist which are linked to the software installed or the set of hardware of the peritoneal dialysis machine. In contrast, it is possible, for example when production errors are made known, to identify all affected peritoneal dialysis machines with a specific software version or a specific set of hardware and to send an automatic message to the technicians to carry out maintenance on that peritoneal dialysis machine.

The number of hours of operation associated with the switching procedures for electromechanical components as well as the fault patterns are analyzed in order to monitor the wear of mechanical/electrical components and if necessary to inform the service personnel SP regarding the imminent replacement of those components. Furthermore, with the hours of operation being known, a reminder regarding the next scheduled maintenance can be sent to the service personnel.

Long-term monitoring of the durational data allows, inter alia, the behavior, wear and robustness of the hydraulic and pneumatic systems of the peritoneal dialysis machine to be analyzed and evaluated.

In this manner, product improvements can be instigated early on.

The data regarding the country for delivery and language of the peritoneal dialysis machine will be extracted, inter alia, in order to draw conclusions regarding problems that are specific to countries, for example relating to extreme climate conditions (temperature, air humidity) or special handling.

Although a wireless or wired data communication network NET1 or NET2 is discussed above, the person skilled in the art will readily recognize that here in particular, a local network up to a global internet network may be meant, wherein all suitable media, such as wire, glass fibre or mobile communications (Bluetooth, ZigBee, WLAN (wireless local area network), GSM (Global System for Mobile Communications), UMTS (Universal Mobile Telecommunications System), LTE (Long-Term Evolution), LTE-A (LTE Advanced) and subsequent technologies are included.

A separation into two (virtual) networks may be advantageous because in this case, direct access to peritoneal dialysis machines and to data regarding the peritoneal dialysis machines stored in the monitoring system 1 can be prevented. This means that unauthorized access can be prevented.

In one embodiment of the invention, a specific evaluation may be requested by a user P, SP, QM, FP.

As described above, at least individual items from the stored data and evaluations of the relevant stored data can be retrieved using a web browser.

In particular, when unsecure communication networks are used, the data for the peritoneal dialysis machine PD1 is advantageously transmitted in an encrypted manner.

In one embodiment of the invention, the messages are sent via a messaging service. This means that the system can be integrated into existing communication infrastructures.

Although the invention has been described above in relation to a peritoneal dialysis machine PD1, the invention is not limited to this, but rather, the monitoring system 1 may monitor a plurality of peritoneal dialysis machines (PD1, PD2 . . . PDn)—as can be seen in FIG. 1.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A monitoring system, wherein the monitoring system comprises a processor and a non-transitory computer-readable medium having processor-executable instructions stored thereon, wherein the processor-executable instructions, when executed by the processor, facilitate:

receiving, by the monitoring system, data from a dialysis machine via a first data communication network, wherein the data includes machine data, error codes, operational data, environmental data, consumables data, network data, and/or treatment data;

storing, by the monitoring system, the received data corresponding to the dialysis machine;

analyzing, by the monitoring system, the stored data corresponding to the dialysis machine to determine a fault with respect to a first component of the dialysis machine;

assigning, by the monitoring system, an error code to the determined fault;

determining, by the monitoring system, a user or user group to which information relating to the fault to is to be sent based on the assigned error code; and sending, by the monitoring system, to the determined user or user group, the information relating to the fault via a second data communication network.

2. The monitoring system according to claim 1, wherein the dialysis machine is a peritoneal dialysis machine.

3. The monitoring system according to claim 1, wherein the first data communication network is a wired data communication network.

4. The monitoring system according to claim 1, wherein the first data communication network is a wireless data communication network.

5. The monitoring system according to claim 1, wherein the second data communication network is a wired data communication network.

6. The monitoring system according to claim 1, wherein the second data communication network is a wireless data communication network.

7. The monitoring system according to claim 1, wherein analyzing the stored data corresponding to the dialysis machine is in response to a user request.

8. The monitoring system according to claim 1, wherein the stored data corresponding to the dialysis machine and a result of the analysis of the stored data corresponding to the dialysis machine are retrievable via a web browser.

9. The monitoring system according to claim 1, wherein the data is received from the dialysis machine in an encrypted manner.

10. The monitoring system according to claim 1, wherein sending the information relating to the fault to the determined user or user group via the second data communication network includes sending a message via a messaging service.

11. The monitoring system according to claim 1, wherein the processor-executable instructions, when executed by the processor, further facilitate:

analyzing, by the monitoring system, the stored data corresponding to the dialysis machine to determine a degree of wear associated with a second component of the dialysis machine.

12. The monitoring system according to claim 11, wherein the second component of the dialysis machine is a membrane pump, and wherein analyzing the stored data corresponding to the dialysis machine to determine a degree of wear associated with the second component of the dialysis machine comprises analyzing changes in pressure and/or channel profile(s) to determine the degree of wear associated with the membrane pump.

13. The monitoring system according to claim 1, wherein the processor-executable instructions, when executed by the processor, further facilitate:

receiving, by the monitoring system, data from a plurality of dialysis machines.

14. The monitoring system according to claim 13, wherein the processor-executable instructions, when executed by the processor, further facilitate:

determining, by the monitoring system, that faults occur with respect to a first dialysis machine more often within a specific time period relative to a second dialysis machine; and requesting, by the monitoring system, additional data from the first dialysis machine based on the determination that faults occur with respect to the first dialysis machine relatively more often.

15. The monitoring system according to claim 1, wherein determining the user or user group to which information relating to the fault to is to be sent based on the assigned error code comprises:

determining whether the information relating to the fault is to be sent to a patient, a medical professional, service personnel or a quality management representative based on the assigned error code.

16. The monitoring system according to claim 15, wherein the information relating to the fault is determined to be sent to service personnel based on the assigned error code corresponding to a fault which requires action by a service technician.

17. The monitoring system according to claim 15, wherein the information relating to the fault is determined to be sent to a quality management representative based on the assigned error code corresponding to a fault related to a lack of user training.

18. The monitoring system according to claim 1, wherein the processor-executable instructions, when executed by the processor, further facilitate:

analyzing, by the monitoring system, the stored data corresponding to the dialysis machine to determine a lack of training with respect to the dialysis machine based on a number of recorded error messages; and sending, by the monitoring system, a notification to a quality management representative regarding the determined lack of training with respect to the dialysis machine.

19. The monitoring system according to claim 1, wherein the processor-executable instructions, when executed by the processor, further facilitate:

analyzing, by the monitoring system, the stored data corresponding to the dialysis machine to determine a lack of training with respect to the dialysis machine based on a length of a time interval between initiating a treatment and commencement of the treatment; and sending, by the monitoring system, a notification to a quality management representative regarding the determined lack of training with respect to the dialysis machine.

* * * * *